(12) United States Patent
Bui et al.

(10) Patent No.: US 6,413,269 B1
(45) Date of Patent: Jul. 2, 2002

(54) STENT DELIVERY SYSTEM

(75) Inventors: Dennis Bui; Jay J. Eum; Paul W. Mikus, all of Irvine, CA (US)

(73) Assignee: Endocare, Inc., Irvine (*) Notice: Subject to any disclaimer, the term of this patent is extended or adjusted under 35 U.S.C. 154(b) by 0 days.

(21) Appl. No.: 09/612,405

(22) Filed: Jul. 6, 2000

(51) Int. Cl.[7] .............................................. A61F 2/06
(52) U.S. Cl. ..................................... 623/1.11; 623/1.12
(58) Field of Search ........................... 623/1.11, 1.12, 623/1.23, 1.13, 1.18, 1.2, 1.22; 606/108, 191, 194, 198

(56) References Cited

U.S. PATENT DOCUMENTS

| | | | |
|---|---|---|---|
| 4,170,990 A | 10/1979 | Baumgart et al. | 128/92 |
| 4,503,569 A | 3/1985 | Dotter | 3/1.4 |
| 4,512,338 A | 4/1985 | Balko et al. | 128/1 |
| 4,553,545 A | 11/1985 | Maass et al. | 128/341 |
| 4,733,665 A | 3/1988 | Palmar | 128/343 |
| 4,762,128 A | 8/1988 | Rosenbluth | 128/343 |
| 4,795,458 A | 1/1989 | Regan | 623/1 |
| 4,913,141 A | 4/1990 | Hillsted | 606/108 |
| 4,969,890 A | 11/1990 | Sugita et al. | 606/192 |
| 5,002,558 A | 3/1991 | Klein et al. | 606/192 |
| 5,019,085 A | 5/1991 | Hillstead | 606/108 |
| 5,037,427 A | 8/1991 | Harada et al. | 606/108 |
| 5,078,736 A | 1/1992 | Behl | 623/1 |
| 5,147,370 A | 9/1992 | McNammara et al. | 606/108 |
| 5,160,341 A | 11/1992 | Brennemen et al. | 606/198 |
| 5,178,618 A | 1/1993 | Kandarpa | 606/28 |
| 5,197,978 A | 3/1993 | Hess | 623/1 |
| 5,224,953 A | 7/1993 | Morgentaler | 606/192 |
| 5,246,445 A | 9/1993 | Yachia et al. | 606/108 |
| 5,306,294 A | 4/1994 | Winston et al. | 623/1 |
| 5,466,242 A | 11/1995 | Mori | 606/198 |
| 5,476,505 A | * 12/1995 | Limon | 623/1 |
| 5,571,135 A | 11/1996 | Fraser et al. | 606/198 |
| 5,772,668 A | 6/1998 | Summers et al. | 606/108 |
| 5,776,141 A | 7/1998 | Klein et al. | 606/108 |
| 5,776,142 A | 7/1998 | Gunderson | 606/108 |
| 5,782,838 A | * 7/1998 | Beyar et al. | 606/108 |
| 5,797,952 A | 8/1998 | Klein | 606/198 |
| 5,816,258 A | 10/1998 | Jervis | 128/898 |
| 5,830,179 A | 11/1998 | Mikus et al. | 604/49 |
| 6,033,413 A | 3/2000 | Mikus et al. | 606/108 |

FOREIGN PATENT DOCUMENTS

| | | |
|---|---|---|
| EP | 0626153 A1 | 11/1994 |
| EP | 0666065 A1 | 8/1995 |
| WO | WO 93/13824 | 7/1993 |

OTHER PUBLICATIONS

Use of Memokath, a second generation urethral stent for relief of urinary retention in male spinal cord injured patients; Paraplegia 32 (1994) 480–488 B M Soni MB MS, et al.

Memokath: A Second Generation of Intraprostatic Spirals; British Journal of Urology; A>L> Poulsen et al.

* cited by examiner

Primary Examiner—David O. Reip
Assistant Examiner—Vy Q. Bui

(57) ABSTRACT

A stent delivery catheter. The catheter includes an inner catheter tube and an outer catheter tube which are rotatable relative to each other. The inner catheter and outer catheter include recesses to receive the ends of the stent, permitting pull wires to engage the stent ends without need to for the pull wires to extend radially beyond the bounds of the catheter or requiring the stent ends to protrude it into the lumen of the inner or outer catheter.

6 Claims, 6 Drawing Sheets

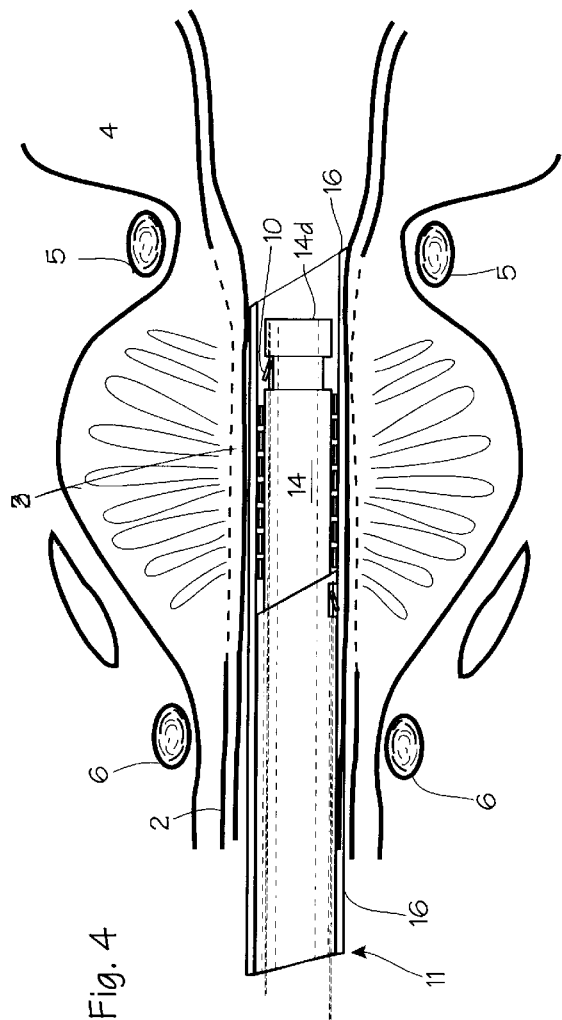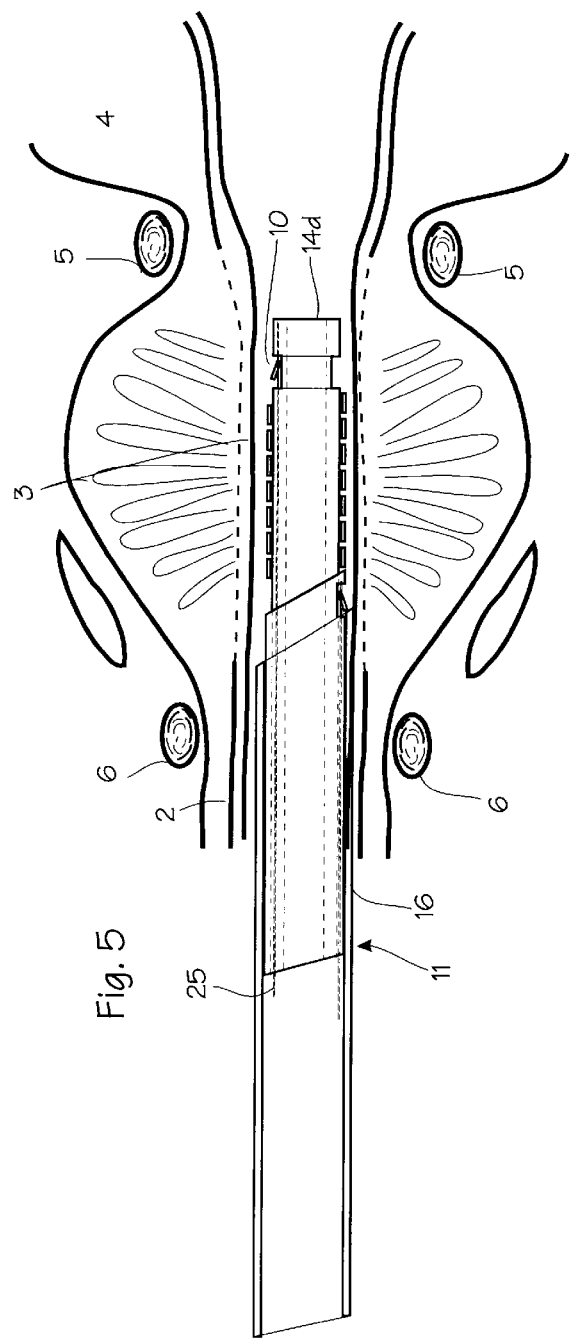

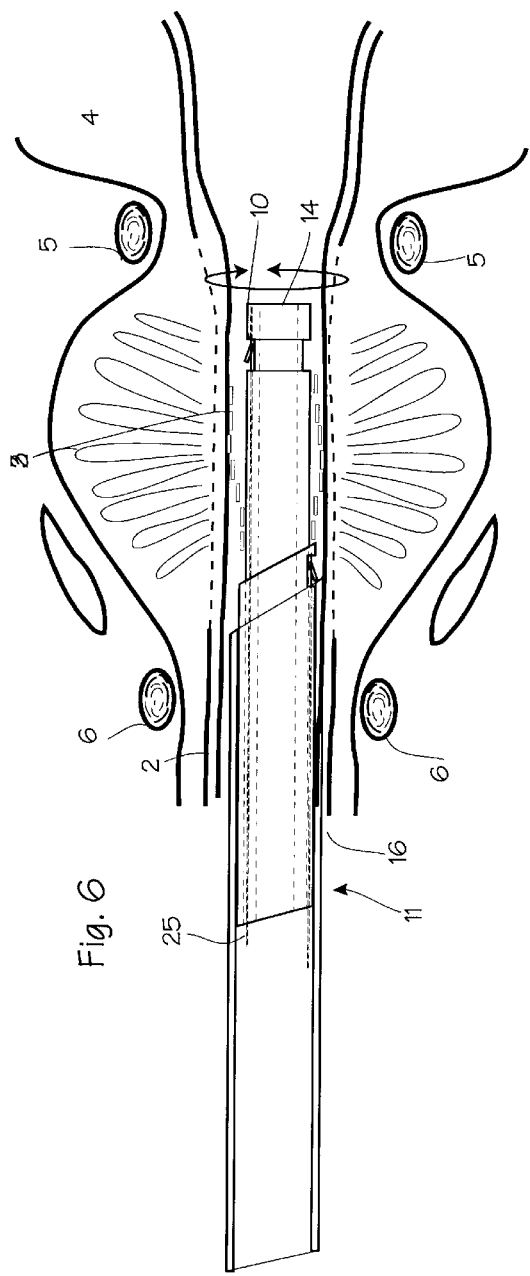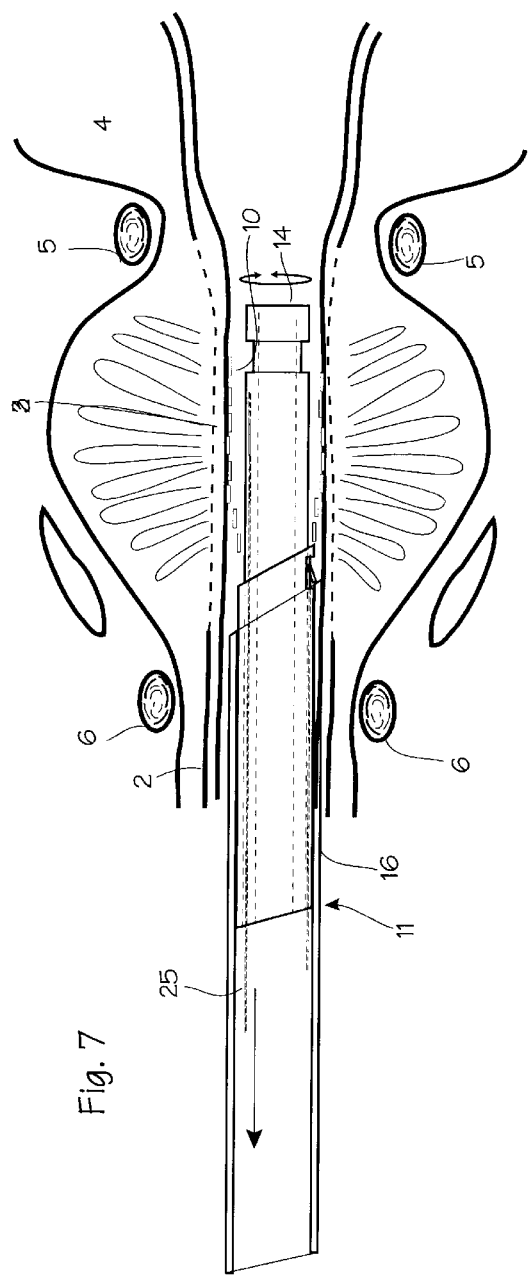

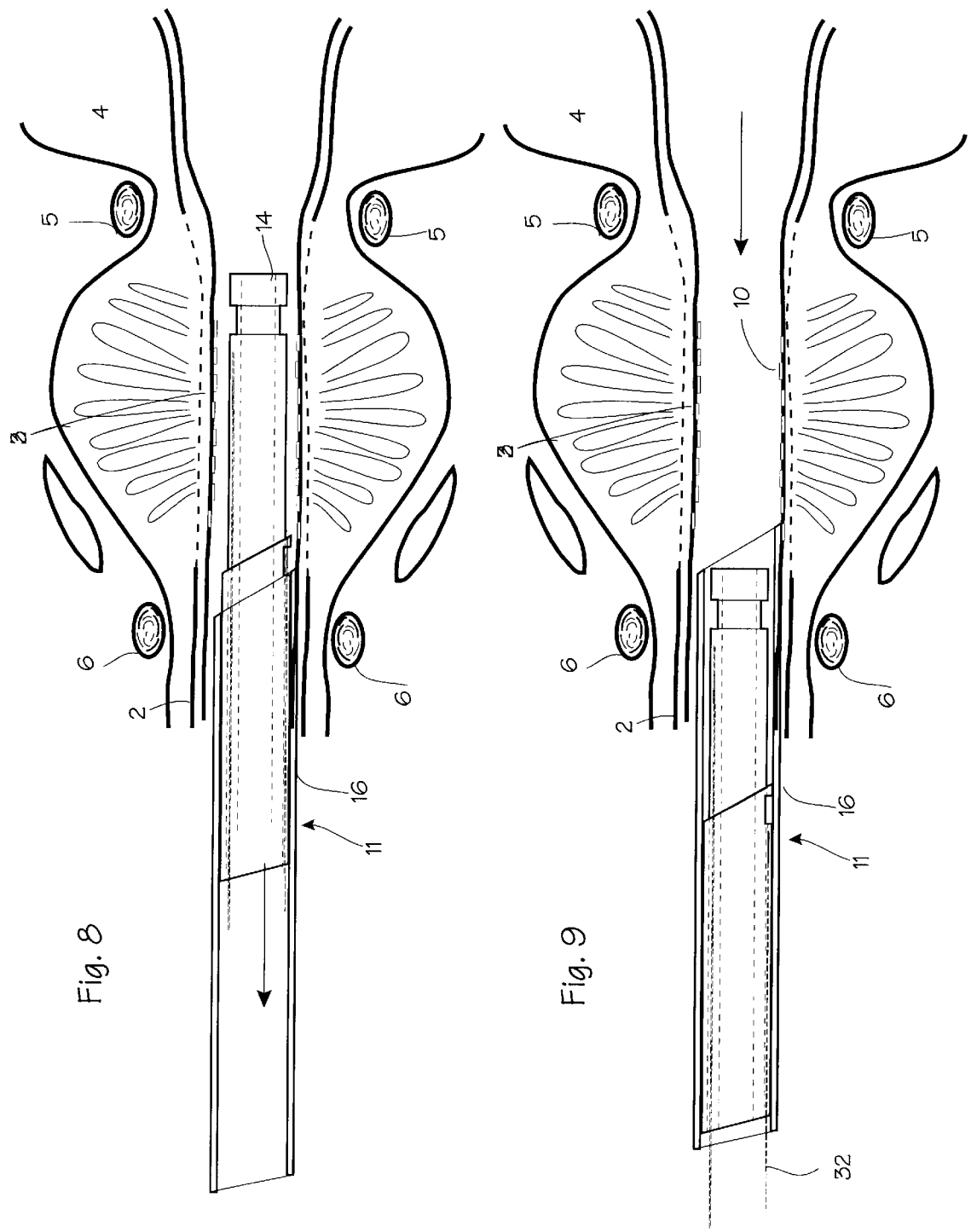

STENT DELIVERY SYSTEM

FIELD OF THE INVENTIONS

This invention relates to stents, urology, and treatments for benign prostate hypertrophy or prostate cancer, as well as methods for correction of vessel occlusions.

BACKGROUND OF THE INVENTIONS

Prostate enlargement, also known as benign prostate hyperplasia or benign prostate hypertrophy, is a common affliction among older men. The condition involves swelling of the prostate. The prostate surrounds the urethra, or urinary tract, and swelling of the prostate prevents passage of urine from the bladder. Benign prostate hyperplasia is uncomfortable because it makes urination difficult or impossible. The condition is also dangerous because it can lead to infection of the bladder and kidneys, and severe cases may lead to death. Prostate cancer is also a common affliction among older men, and may lead to many of the same symptoms as benign prostate enlargement. Prostate cancer is more dangerous in that it may spread to other organs and is often fatal. Early treatment can reduce the risks of death due to prostate cancer.

Both prostate enlargement and prostate cancer can be treated with heat treatments such as hyperthermia or thermotherapy. As described in our co-pending U.S. application Ser. No. 08/629,650 filed Apr. 9, 1996, a stent serves the dual purpose of acting as a heat source for the thermotherapy procedures, as well as acting to hold the urethra open after therapy to prevent blockage due to swelling and prostate tissue sloughing. A stent may be implanted as an interim solution to hold open the urethra while the patient awaits more aggressive surgery or treatment. A stent may be implanted after hypothermia or cryosurgery to keep the urethra open while enlargement subsides. Finally, a stent may be implanted as a primary treatment.

When the stent is implanted for any of these reasons, it is usually better to leave the bladder neck sphincter and the external sphincter un-blocked by the stent. These sphincters control the flow of urine through the urethra, and if the stent is placed within these sphincters they will not be able to close. This would leave the patient incontinent. To ensure the proper positioning of the stent, the devices below provide several benefits including controlled release of the stent, tentative initial opening of the stent, and visualization of the bladder and prostatic urethra during placement.

McNamara, et al., Nitinol Stent For Hollow Body Conduits, U.S. Pat. No. 5,147,370 (Sep. 15, 1992) describes a catheter delivery system which uses a single pullwire to retain and release a stent wrapped on the distal end of a catheter. The stent must be provided with "retaining means" in the form of pigtails or hooks on the stent ends capable of engaging a pullwire. The catheter must have two holes communicating into a lumen within the catheter, and the stent ends must enter the lumen through the holes. The pullwire is in the lumen, and engages the stent ends which enter the lumen. After release into the lumen, the retaining means are left to hang in the body lumen. This could lead to thrombus formation in blood vessels and undesirable deposition in urethral stents unless addition precautions are taken to avoid the complications. While materials may be developed in which the stent retaining pigtail structures are not set into the form of the stent, common stent alloys such elgiloy, nitinol and stainless steel will take a set in the form of pigtails if deformed as suggested by McNamara.

Hillstead, Apparatus And Method For Placement Of A Stent Within A Subject Vessel, U.S. Pat. No. 4,913,141 (Apr. 3, 1990) discloses a stent delivery device which uses a pullwire running through the central lumen of the catheter and exiting the catheter to run over the stent ends. The stent is deployed by pulling the pullwire proximally, requiring the pullwire to course over intimal and endothelial surfaces of the body lumen to be treated. This could lead to damage of lumenal surfaces and attendant healing responses which are undesirable. Neither McNamara nor Hillstead provide a mechanism which permits retention and release of the stent with a mechanism which remains in the annular space of the stent, and do not present radially extending features such as the radially outwardly protruding pullwires or radially inwardly protruding pigtails.

SUMMARY

The stent delivery systems described below permit placement of stents in the urethra and other body vessels. The devices are intended to deploy a shape memory stent or other resilient stent into the prostatic urethra under direct vision. The surgeons who use the stent delivery systems can easily place the stent within the prostatic urethra and make sure that the stent does not block the bladder neck sphincter. The stent is retained on the catheter with a retaining wire or rod which engages the stent ends as the stent ends protrude into recesses in the catheter walls. The catheter is comprised of two coaxial tubes, one inside the other, and the distal end of the stent is secured to the inner tube while the proximal end of the stent is secured to the outer tube. When both ends of the stent are secured to their respective tubes, the tubes may be rotated relative to each other to open the stent or tighten the stent. The stent may be released from the catheter by pulling the pull wires proximally out of engagement with the stent ends. The pull wire which retains the distal end of the stent is release first, and the location of the distal end of the stent is observed. Once the distal end of the stent is located properly, the proximal end of the stent is released from the catheter by pulling the pull wire which retains the proximal end of the stent out of engagement with the proximal end of the stent.

BRIEF DESCRIPTION OF THE DRAWINGS

FIG. 4 illustrates initial insertion of the stent delivery system into the prostatic urethra.

FIG. 5 illustrates the procedure of installing the stent in the prostatic urethra.

FIG. 6 illustrates the procedure of installing the stent in the prostatic urethra.

FIG. 7 illustrates the procedure of installing the stent in the prostatic urethra.

FIG. 8 illustrates the procedure of installing the stent in the prostatic urethra.

FIG. 9 illustrates the procedure of installing the stent in the prostatic urethra.

DETAILED DESCRIPTION OF THE INVENTIONS

Figure 1:
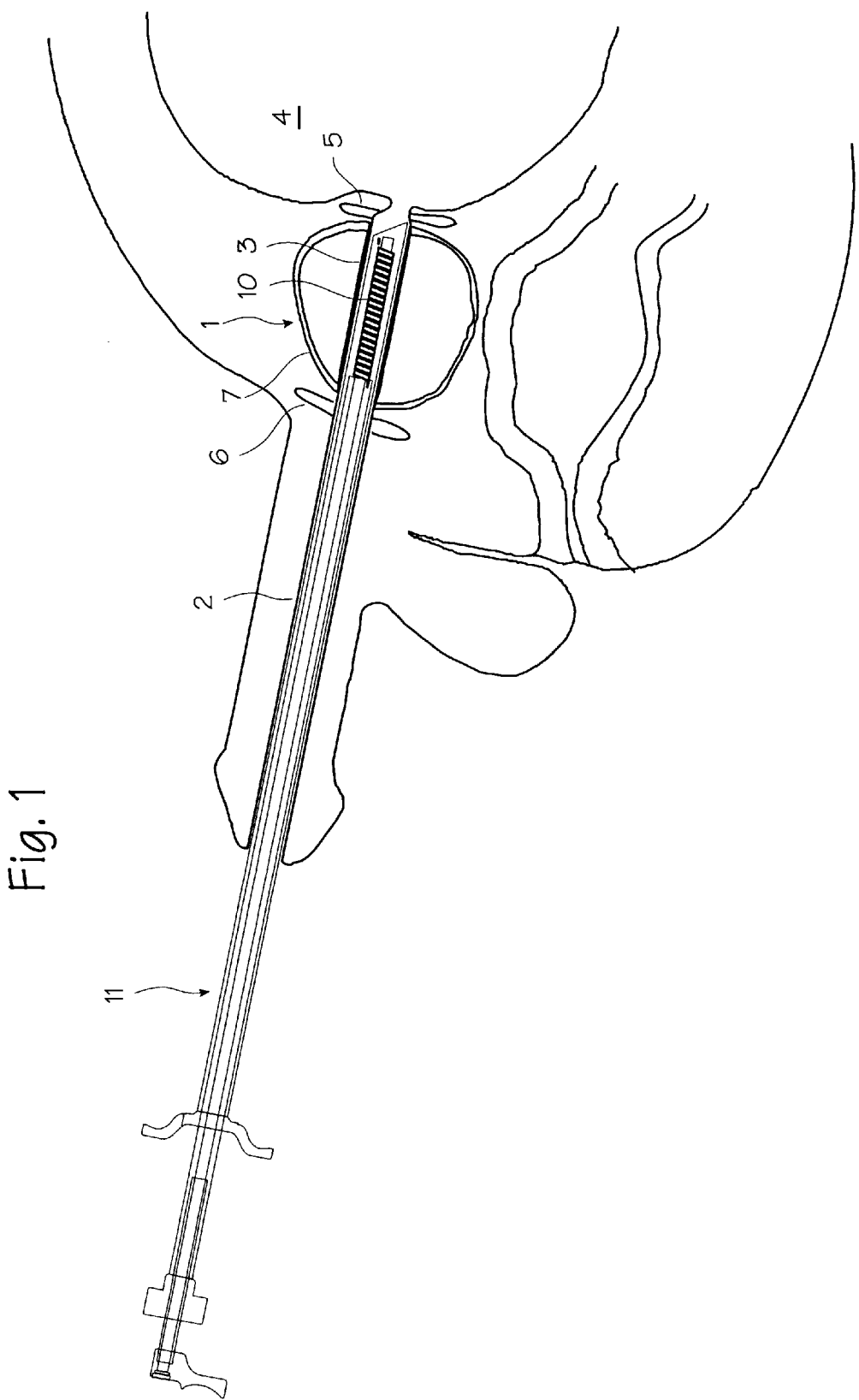
FIG. 1 illustrates a use of the stent delivery system in the treatment of prostate disease.

FIG. 1 shows an overview of a procedure for which the stent and stent delivery system may be used in the treatment of benign prostate hyperplasia or prostate cancer. The details of the local anatomy shown in this figure include the prostate gland 1, the urethra 2 and the prostatic urethra 3. The urethra is the channel which conducts urine from the bladder 4 to the penis for discharge from the body. The prostatic urethra is a continuation of the urethra, and it joins the prostate gland to the urethra. The bladder neck sphincter 5 controls flow of urine from the bladder 4, and the external sphincter 6 controls flow of urine or ejaculate from the bladder 4 or prostate 1. The prostate capsule 7 surrounds the prostate gland. The prostate gland consists of various tissues, including glandular tissue (which produces ejaculate), muscular cells, and epithelial cells. The inside diameter of urethra 2 is typically about 2 centimeters, and the prostatic urethra varies in length from about 15 to 75 mm.

The condition of benign prostate hyperplasia causes the prostate to swell and close off the prostatic urethra. The prostatic urethra 3 is squeezed shut by the swollen prostate, and has an occluded region which must be treated. The stent 10 mounted on the distal portion of delivery catheter 11 is shown ready for placement in the occluded portion of the prostatic urethra. The stent is positioned and released within the prostate through the operation of the delivery catheter as described below. The delivery catheter illustrated in FIG. 1 is rigid, so that the urethra has conformed to the straight configuration of the delivery catheter.

The stent is made of a nitinol alloy with a martensite transition temperature slightly below body temperature, in the range of 30–35° C. (86–95° F.) (this range is conveniently established or maintained with cold saline flow through the catheter or a catheter sheath). Thus, when the stent is cooled below body temperature by cold saline flow, it will enter the soft and pliable martensite state of the alloy. The chosen alloy has a wide hysteresis, so that it remains in the soft and pliable martensite state for a temperature range distinctly above the temperature at which it converts to martensite upon cooling. The transition temperature for the change to the austenitic state upon heating may be varied. It may be just below body temperature, so that warming to body temperature is sufficient to induce reversion to the memorized large diameter configuration. If heating sources are used, the transition temperature may be slightly above body temperature, in the range of 38–60° C. (100–140° F.) or even higher, depending on the heating source used. When hot saline solution is used, 38–60° C. is convenient because that temperature range can be easily achieved by flushing hot saline through the catheter into the vicinity of the stent (100° C. is the equivalent to 212° F., the boiling point of water, so it can be appreciated that the temperature range of 38–60° C. is easily achieved in the operating room). Other stent materials may be used in conjunction with the delivery system such as stainless steel, plastics, elgiloy and other resiliently deformable materials. Even plastically deformable stent materials such as tantalum may be used.

Figure 2:
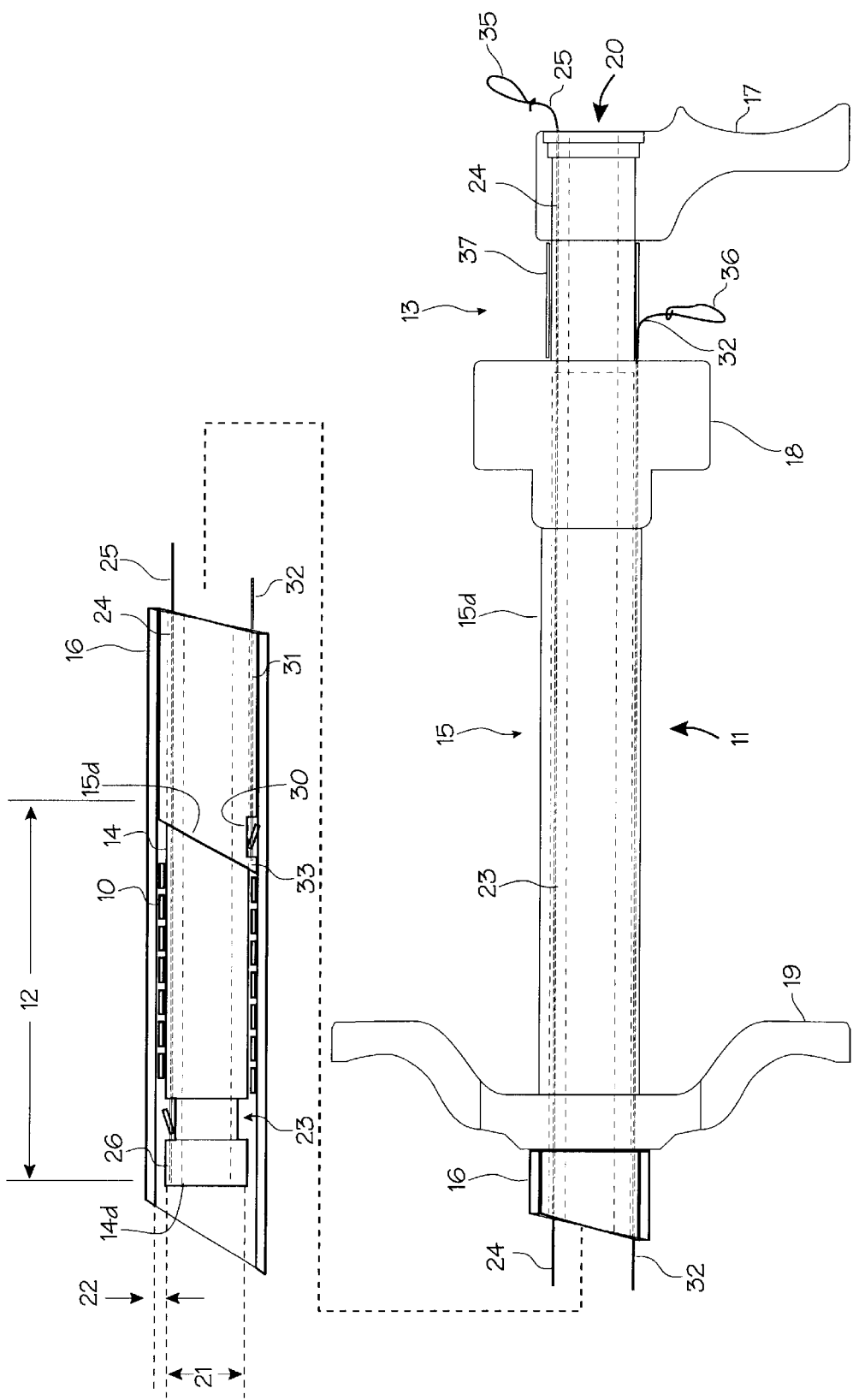
FIG. 2 is a cross section of the stent delivery system.

FIG. 2 illustrates the stent delivery system. The stent 10 is mounted on the delivery catheter 11 in the distal portion referred to as the stent loading zone 12. The catheter is controlled and the stent is released through operation of the operating mechanism in the proximal end 13 of the delivery catheter. The delivery catheter is comprised of an inner catheter 14 and an outer catheter tube 15 disposed coaxially over the inner catheter, and a sheath 16 coaxially disposed over both the inner catheter and the outer catheter tube. The outer catheter tube and inner catheter are rotatable relative to each other about the longitudinal axis of the catheter, and may be rotated using the proximal handle 17 mounted on the proximal end of the inner catheter and proximal handle 18 mounted on the proximal handle of the outer catheter tube. The inner catheter and outer catheter tube may also slide longitudinally relative to one another. The sheath 16 may also slide relative to the inner catheter and outer catheter tube, and may be operated with the proximal sheath handle 19. The sheath 16 may be rotatable as in the embodiment shown, where no structure inhibits rotation. Alternatively, the sheath may be rotationally fixed relative to either the inner catheter or outer catheter tube, with, or example, a longitudinally oriented tongue and groove structure or spline and keyway structure mating the sheath to the outer catheter tube.

The inner catheter may be a substantially solid cylinder or it may be a hollow tube, in which case it may accommodate an endoscope for viewing the prostatic urethra and stent location before the stent is released. The endoscope lumen 20 shown in FIG. 2 has an diameter approximating common endoscopes. The inner catheter, outer catheter and sheath may be made of a transparent plastic or glass so that anatomical landmarks of the prostatic urethra may be seen through the catheter. The components may be rigid, and comprised of stiff transparent plastic such as polyethylene terepthalate (PET) which facilitates placement in the urethra, but may be made of a flexible transparent material for placement in other areas of the body where flexibility will facilitate placement. The overall length of the delivery system may be about 35 cm (about 14 inches) when constructed for placement of the stent in the urethra.

The inner catheter diameter 21 at the loading zone 12 is chosen such that, when the stent is wrapped tightly about the distal tip, the overall diameter of the inner catheter and stent is the same as the outer diameter of the outer catheter tube. In other words, the inner catheter has an outer diameter equal to the outer catheter tube minus twice the stent thickness 22, and the combined inner catheter and stent are isodiametric with the outer catheter tube. The inner diameter of the outer catheter tube is chosen to provide snug but slidable and rotatable fit over the inner catheter, at least near the loading zone. The inner diameter of catheter sheath 16 is chosen to provide snug but slidable and rotatable fit over the outer catheter and stent.

Near the distal tip 14d of the inner catheter 14, an annular recess 23 or notch is formed in the outer wall. The recess or notch does not extend entirely through the catheter wall. In the embodiment shown, the annular recess extends to a depth equal to or greater than the stent thickness. Cut-outs or holes extending entirely through the catheter wall may be used in lieu of the recess or notch. The inner catheter has a side lumen 24 which passes from the distal end of the catheter, at least from the annular recess proximally to the proximal end of the delivery system. The side lumen opens into the annular recess 23. A first pullwire 25, disposed within a side lumen of the inner catheter, extends from the proximal end of the delivery system to the annular recess. The pullwire extends further distally to engage the stent, and, optionally, into the distal extension 26 of the pullwire lumen beyond the annular recess. The pullwire engages a hole 27 or hook in the distal end of the stent (visible in FIG. 3), and thereby retains the distal end of the stent 10 to the distal end 14d inner catheter. The pullwire is preferably sufficiently stiff and rigid to be both pull and pushed within the pull wire lumen, so that the stent may engaged within the recess to re-engage the stent with the delivery system in order to remove the stent or adjust its position after placement.

Near the distal tip 15d of the outer catheter 15, an annular recess 30 or notch is formed in the outer wall. As with the inner catheter recess, the recess or notch does not extend entirely through the catheter wall. In the embodiment shown, the annular recess extends to a depth equal to or greater than the stent thickness. Cut-out or holes extending entirely through the catheter wall may be used in lieu of the recess or notch. The outer catheter has a side lumen 31 which passes from the distal end of the catheter, at least from the annular recess proximally to the proximal end of the delivery system. The side lumen opens into the annular recess. A second pullwire 32, disposed within a side lumen of the outer catheter, extends from the proximal end of the delivery system to the annular recess. The pullwire extends further distally to engage the stent, and, optionally, into the distal extension 33 of the pullwire lumen beyond the annular recess. The second pullwire engages a hole 34 or hook in the proximal end of the stent (visible in FIG. 3), and thereby retains the proximal end of the stent to the distal end 15d of the outer catheter tube. Again, the pullwire is preferably sufficiently stiff and rigid to be both pull and pushed within the pull wire lumen, so that the stent may engaged within the recess to engage the stent.

Referring now to the proximal end of the stent delivery catheter, the first and second pull wires exit their respective lumens and terminate in pull rings 35 and 36 which can be used to pull the pullwires proximally. When the pullwires are pulled proximally, the ends of the stent which they hold in the annular recesses are released. Interposed between the inner catheter handle 17 and the outer catheter handle 18 is a collet 37. The collet serves to lock the inner catheter and outer catheters longitudinally in relation to each other until longitudinal movement is desired. When movement is desired, the collet is easily removable, and is provided with a longitudinal slit to permit easy removal by the operator during surgery.

The stent delivery system is assembled by wrapping a helical stent around the distal end of the inner catheter tube and placing the distal end of the stent in the recess of the inner catheter tube and placing the proximal end of the stent in the recess of the outer catheter. The stent is secured on the stent delivery system by passing the first retaining wire longitudinally through the wall of the inner catheter tube to enter the recess of the inner catheter tube and engage the distal end of the stent within the recess, and then passing a second retaining wire longitudinally through the wall of the outer catheter to enter the recess of the outer catheter and engage the proximal end of the stent within the recess. The sheath is then slipped over the entire assembly. If the stent is a nitinol or shape memory alloy or polymer susceptible to superelastic behavior, it is best to assemble the device while maintaining the stent below the superelastic temperature range or the shape recovery transition temperature.

Figure 3:
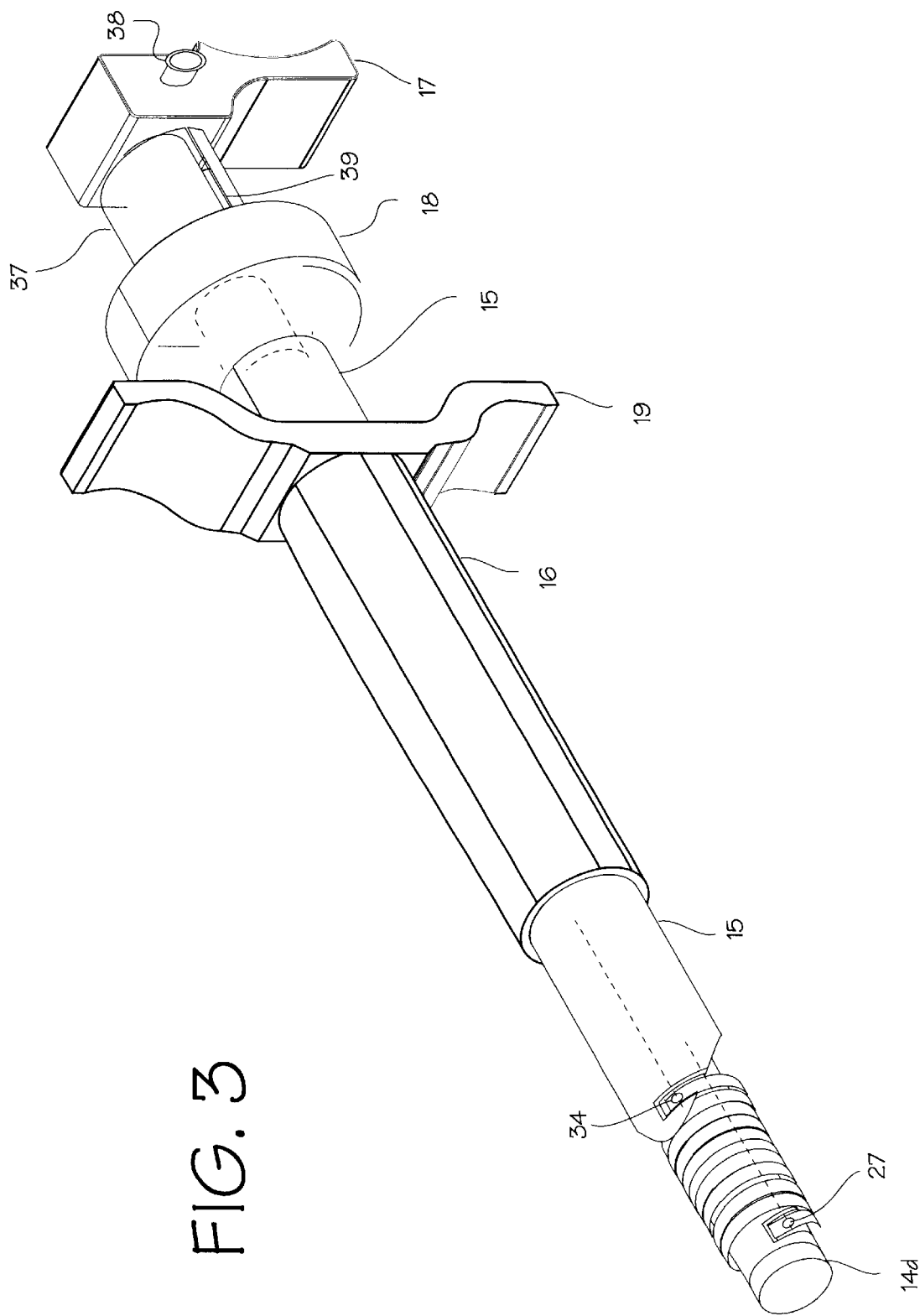
FIG. 3 is an elevational view of the stent delivery system.

FIG. 3 is an elevational view of the stent delivery system. In this view, additional features are visible. The proximal handle 17 for the inner catheter tube 14 is fitted with two leur fittings 38 (only one is visible in this view) which permit injection of fluids as required during the procedure. The slit 39 of collet 37 permits easy installation and removal. At the distal end of the delivery catheter, the disposition of the stent distal and proximal end in the recesses 23 and 30 is visible. The pullwires do not need to exit the catheter lumen to engage the stent, and do not pass radially through the catheter wall in order to engage the stent. Additionally, the stent ends to not need to enter the lumen of either the inner catheter or the outer catheter in order to engage with the pullwires, and there is no need for cut-outs in the catheter walls to allow passage of the stent ends into the interior of the catheter. Indeed, the outer catheter lumen is taken up completely by the diameter of the inner catheter, so that the stent ends cannot enter this lumen.

FIGS. 4 through 8 depict placement of the stent. FIG. 4 illustrates initial insertion of the stent delivery system into the prostatic urethra. The surrounding anatomy is shown in a frontal view, and corresponds to the anatomy shown in FIG. 1. The stent has been tightly wound on the stent loading zone of delivery catheter 11, and has a small diameter of about 0.75 to 1 cm (0.25 to 0.40 inches) that fits easily into the urethra 2. When coiled for insertion, the stent is about 4.5 cm (1.75 inches) long. The catheter sheath 16 is provided to cover the stent during placement and provide a smooth outer surface to facilitate placement of the stent. The delivery system is then pushed through the urethra until the stent is located in the prostatic urethra 3, as shown in FIG. 4. An endoscope is placed within the lumen of the inner catheter so that correct initial placement may be verified visually. Preferably, the operator will insert the catheter until distal end of the sheath is aligned with bladder neck or about 0.25 cm short of the bladder neck. This will locate the stent delivery zone of the catheter between the bladder neck sphincter 5 and the external sphincter 6 inside the prostatic urethra 3.

The next step of the procedure is illustrated in FIG. 5. Having visually confirmed the position of the stent, the operator pulls the sheath 16 proximally until the stent 10 and the distal tip 14d of the inner catheter 14 is exposed. The stent, along with the inner catheter and outer catheter tube, are maintained in position by holding the proximal handles in place while the sheath handle 19 (shown in FIG. 2) is pulled proximally. Next, as illustrated in FIG. 6, the inner catheter 14 is rotated (using the proximal handle 17, shown in FIG. 2) relative to the outer catheter tube 15. This forces the stent to open partially (the proximal and distal ends of the stent are still attached to the delivery system via the pull wires) and partially engage the prostatic urethra 3. The operator may visually confirm the location of the stent and proper opening of the stent through the endoscope. If the stent location is not acceptable, the stent is flushed with cold saline to bring the stent temperature down to the martensite range. This softens the stent, making it pliable and easily re-tightened on the stent loading zone by rotating the inner catheter in the tightening direction. The cold stent is then tightened on the inner catheter by rotating the inner catheter relative to the outer catheter.

When the stent location is acceptable, the distal end of the stent may be released as illustrated in FIG. 7. The pullwire 25 in the inner catheter is pulled proximally and out of engagement with the distal end of the stent. The distal end of the stent is then released to engage the prostatic urethra. Again, the position of the stent may be visually checked through the endoscope, by viewing through the inner catheter wall. If the stent is not properly located, it is preferable to cool it with cold saline to soften, it pull it into the outer sheath and remove it from the body. The procedure can be repeated with a replacement delivery system or the stent can be reloaded on the catheter and re-used where appropriate.

With the stent partially released and properly located, the proximal end of the stent may be released as illustrated in FIG. 8. The operator pulls the pullwire 32 proximally, out of engagement with the proximal end of the stent, and the proximal end of the stent is released to expand into engagement with the prostatic urethra. When fully released, the stent will expand radially up to about 1 cm (0.4 inches) and contract longitudinally (foreshorten) to about 2.5 centimeters (one inch) in length. The actual diameter and length of the stent within the prostatic urethra will vary according to the physical condition of the prostatic urethra, the physical attributes of the stent, and the manipulation by the operator.

After placement of the stent, all components of the delivery system are withdrawn from the urethra, as illustrated in FIG. 9 and the stent insertion procedure is complete.

After placement in a swollen prostate, as depicted in FIG. 9, the stent will be firmly held by the compressive forces of the prostate. The stent may be flushed with hot saline to cause the stent to heat up well above its austenite transition temperature. Of course, if the stent transition temperature is at or below body temperature, it will be sufficient to allow the stent to be heated to the austenite transition temperature by surrounding body temperature without injection of warm saline solution. The stent may be left in the urethra for some time, either as a temporary palliative for prostate ablation or it may remain in place permanently with due care taken to avoid infection.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A stent delivery catheter for delivering a stent into a lumen of the body, wherein said stent has a distal end and a proximal end and a small diameter insertion configuration, said stent delivery catheter comprising:

a first tube having a distal end and a proximal end, said first tube characterized by a tube wall, a central lumen, and at least one side lumen extending from the distal end to the proximal end thereof;

a second tube having a distal end and a proximal end, said second tube characterized by a tube wall, a central lumen, and at least one side lumen extending from the distal end to the proximal end thereof, said second tube being coaxially disposed over the first tube, said distal end of the second tube terminating proximally of the distal end of the first tube;

a third tube having a distal end and a proximal end, said third tube being coaxially disposed over the second tube;

said first and second tubes being rotatable relative to each other;

said third tube being longitudinally slidable relative to the first and second tubes;

wherein the distal end of first tube has a recess extending from the outer surface of the first tube wall at least partially through the wall of the first tube and to a depth sufficient to communicate with the side lumen of the first tube, said recess adapted to receive the distal end of the stent;

wherein the distal end of second tube has a recess extending from the outer surface of the second tube wall at least partially through the wall of the first tube and to a depth sufficient to communicate with the side lumen of the first tube, said recess adapted to receive the proximal end of the stent;

a first retaining wire disposed within the side lumen of the first tube, said first retaining wire extending from the proximal end of the first tube to the distal end of the first tube and being longitudinally translatable within the side lumen so as to be capable of extending into the recess of the first tube;

a second retaining wire disposed within the side lumen of the second tube, said second retaining wire extending from the proximal end of the second tube to the distal end of the second tube and being longitudinally translatable within the side lumen so as to be capable of extending into the recess of the second tube.

2. The stent delivery catheter of claim 1 wherein the length of the stent delivery catheter extending from the recess of the first tube and the recess of the second tube comprise a stent loading segment of the delivery catheter, said stent delivery catheter further comprising:

a helical self-expanding stent having a large diameter when unconstrained and capable of being deformed into a small diameter insertion configuration, said stent having a distal end and a proximal end;

said stent being deformed into its insertion configuration and disposed coaxially over the stent loading segment, the distal end the stent extending into the recess of the first tube and the proximal end of the stent extending into the recess of the second tube;

wherein the first retaining wire extends into the recess of the first tube to engage the distal end of the stent and the second retaining wire extends into the recess of the second tube to engage the proximal end of the stent.

3. The stent delivery catheter of claim 1 wherein:

the outer diameter of the second tube is greater than or equal to the outer diameter of the stent in its insertion configuration.

4. The stent delivery catheter of claim 2 wherein:

the outer diameter of the stent in its insertion configuration is smaller than or equal to the outer diameter of the second tube.

5. A method for assembling a stent delivery catheter comprising:

providing a stent delivery catheter comprising a first tube and second tube, said first tube being coaxially disposed within the second tube and extending distally from the distal end of the second tube, wherein said first and second tubes each have a recess near the distal end thereof;

wrapping a helical stent around the distal end of the first tube and placing the distal end of the stent in the recess of the first tube and placing the proximal end of the stent in the recess of the second tube;

passing a first retaining wire longitudinally through the wall of the first tube to enter the recess of the first tube and engage the distal end of the stent within the recess;

passing a second retaining wire longitudinally through the wall of the second tube to enter the recess of the second tube and engage the proximal end of the stent within the recess;

providing a third tube and sliding the third tube coaxially over the first and second tubes and the stent.

6. A method for assembling a stent in a lumen of the body, said method comprising:

providing a stent delivery catheter comprising a first tube and second tube, said first tube being coaxially disposed within the second tube and extending distally from the distal end of the second tube, wherein said first and second tubes each have a recess near the distal end thereof;

wrapping a helical stent around the distal end of the first tube and placing the distal end of the stent in the recess of the first tube and placing the proximal end of the stent in the recess of the second tube;

passing a first retaining wire longitudinally through the wall of the first tube to enter the recess of the first tube and engage the distal end of the stent within the recess;

passing a second retaining wire longitudinally through the wall of the second tube to enter the recess of the second tube and engage the proximal end of the stent within the recess;

providing a third tube coaxially disposed over the first and second tubes and the stent;

inserting the distal end of the stent delivery system including the stent into the body;

pulling the third tube proximally to expose the stent and the distal end of the first tube within the body;

rotating the first tube relative to the second tube to at least partially open the stent;

pulling the first retaining wire proximally to release the distal end of the stent;

pulling the second retaining wire proximally to release the proximal end of the stent.

* * * * *